United States Patent [19]

Lukacs et al.

[11] Patent Number: 5,032,581
[45] Date of Patent: Jul. 16, 1991

[54] TYLOSIN DERIVATIVES

[75] Inventors: Gabor Lukacs; Catherine Ruggeri-Duchatelle, both of Paris; Aimee Dessinges, Orleans; Alain Olesker, Gif-Sur-Yvette; Maria Laborde, Paris; Li Ming, Gif-Sur-Yvette, all of France

[73] Assignee: Adir Et Cie, Neuilly-sur-Seine, France

[21] Appl. No.: 419,826

[22] Filed: Oct. 11, 1989

[30] Foreign Application Priority Data

Oct. 27, 1988 [FR] France ................. 88 14004

[51] Int. Cl.$^5$ ................. C07H 31/70; C07H 17/08
[52] U.S. Cl. ........................... 514/30; 536/7.1
[58] Field of Search ................. 536/7.1; 514/30

[56] References Cited

U.S. PATENT DOCUMENTS 4,918,058  4/1990  Lukacs et al. ................. 514/30

FOREIGN PATENT DOCUMENTS 0087921   9/1983  European Pat. Off. ............ 536/7.1
0287082  10/1988  European Pat. Off. ............ 536/7.1

OTHER PUBLICATIONS

Fujiwara et al., Chemical Abstracts, vol. 107, (1987) p. 697, No. 7519r.

Umezawa et al., Chemical Abstracts, vol. 108, (1988) p. 754, No. 187201e.

Sakakibara et al., Chemical Abstracts, vol. 90 (1979) p. 550, No. 138149v.

*Primary Examiner*—Elli Peselev
*Attorney, Agent, or Firm*—Gordon W. Hueschen

[57] ABSTRACT

Compounds of general formula:

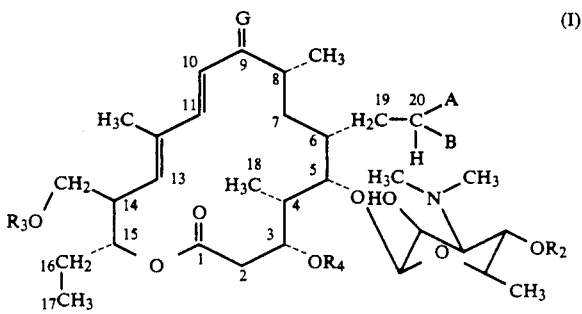

where A, B, G, $R_2$, $R_3$, $R_4$ and ⌇ are defined in the description.

Medicinal products comprising a compound of the invention and useful in the treatment of bacterial infections are also disclosed.

10 Claims, No Drawings

TYLOSIN DERIVATIVES

The present invention relates to new antibiotics of the macrolide family, to a process for preparing them and to pharmaceutical compositions containing them.

The requirements of therapeutics demand the constant development of new antibiotics, not only on account of the possibility of the appearance of new resistant strains, but also with the object of creating new molecules possessing improved activity in respect of both their threshold of efficacy and the breadth of their spectrum of action.

A large number of modifications of the tylosin ring-system have already been carried out in order to produce advantageous antibiotics. Among the most recent, U.S. Pat. Nos. 4,528,369, 4,581,346 and 4,629,786 and European Patent Applications 0,103,465, 0,104,028, 0,154,495 and 0,203,621 may be mentioned. However, none of these modifications has enabled a tylosin derivative used in human therapy to be obtained.

More especially, the subject of the present invention is the compounds derived from tylosin of general formula:

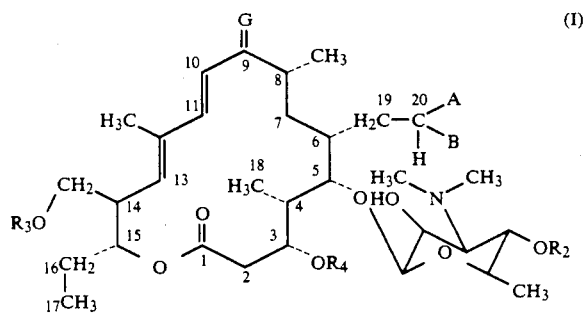

in which:
either:
A denotes a group

in which D and E, which may be identical or different, denote, independently of one another, a hydrogen atom or a linear or branched lower alkyl radical optionally substituted with a phenyl group, and in this case B denotes a cyano group,
or alternatively:
A and B together denote a group $=N^+(O^-)-D$ in which D has the meaning as above,
G denotes an oxygen atom or a group of formula

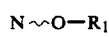

in which $R_1$ denotes a hydrogen atom, a linear or branched lower alkyl group or a linear or branched lower alkenyl group, the latter groups optionally being substituted with a phenyl group which is itself optionally substituted with a nitro group,
the sign ∼ occurring in the definition of G meaning that the oxime or oxime ether group can be in the syn or anti form or in the form of a syn/anti mixture, $R_2$ denotes
either a hydrogen atom,
or a radical of formula:

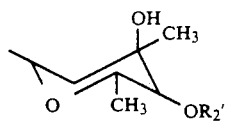

in which $R'_2$ denotes a hydrogen atom, a linear or branched lower alkyl radical or a linear or branched lower acyl radical,
$R_3$ denotes a hydrogen atom or a group:

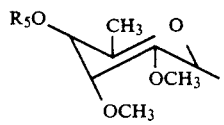

and
$R_4$ and $R_5$ denote, independently of one another:
either a hydrogen atom,
or a linear or branched lower alkyl radical.

Lower alkyl and lower alkenyl radicals are understood to mean groups comprising between 1 and 6 carbon atoms.

The invention also encompasses the salts of the compounds of formula (I). Among acids which may be added to the compounds of formula (I) to form an addition salt, hydrochloric, hydrobromic, hydriodic, sulfuric, acetic, propionic, trifluoroacetic, maleic, malic, tartaric, methanesulfonic, ethanesulfonic, benzenesulfonic, ptoluenesulfonic, phosphoric, fumaric, citric and camphoric acids, etc., may be mentioned by way of example.

The present invention also encompasses a process for preparing the derivatives of formula (I), wherein a derivative of formula (II):

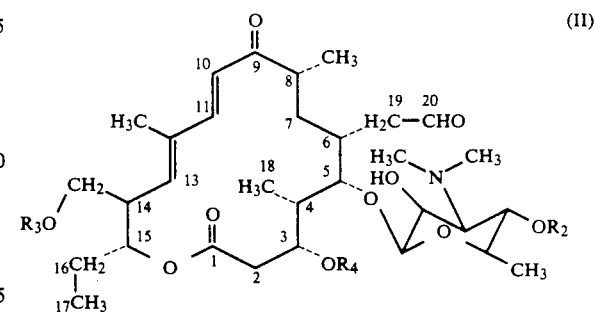

in which $R_2$, $R_3$ and $R_4$ have the same definition as in the formula (I), is used as starting material, which derivative, in the case where $R_2$ denotes a hydrogen atom in the product of formula (I) which it is desired to obtain, is first subjected to the action of dilute hydrochloric acid of normality between 0.05 and 0.4, preferably between 0.1 and 0.30 and preferably between 0.15 and 0.25, at room temperature, to lead, after washing with a suitable organic solvent, alkalinization and extraction with a suitable organic solvent, to a derivative of formula (II/2a):

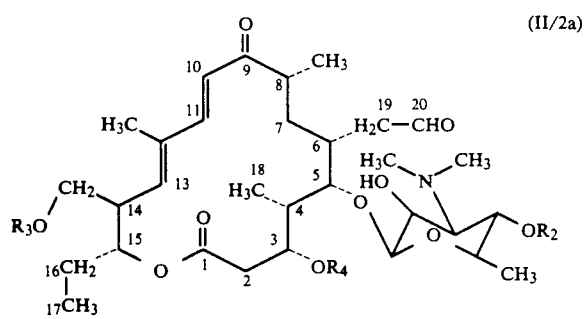
(II/2a)

in which R₃ and R₄ have the same meaning as in the formula (I), which, in the case where R₂ and R₃ simultaneously denote a hydrogen atom in the product of formula (I) which it is desired to obtain, is next subjected to reaction with dilute hydrochloric acid of normality between 0.25 and 0.75, preferably between 0.3 and 0.7 and preferably between 0.4 and 0.6, at a temperature preferably between 30° and 100° C., preferably between 50° and 90° C. and preferably between 70° and 80° C., to lead, after washing with a suitable organic solvent, alkalinization and extraction with a suitable organic solvent, to a derivative of formula (II/2b):

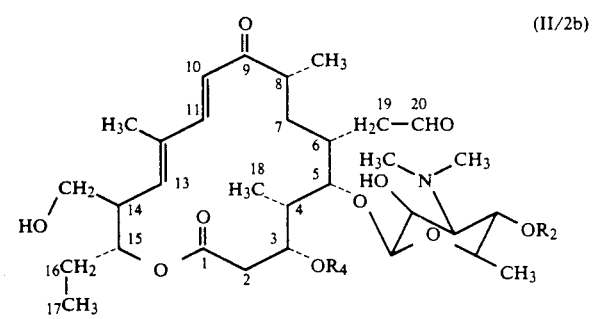
(II/2b)

in which:

R₄ has the same meaning as in the formula (I), which is optionally purified by chromatography on a silica column, the compounds accordingly selected, of general formula (II) or (II/2a) or (II/2b) depending on the compound of formula (I) which it is desired to obtain, then being treated:

either, in the case where B denotes a cyano group, with a dialkyl cyanophosphonate such as diethyl cyanophosphonate, in the presence of an amine of formula (III) HNDE where D and E have the same meaning as in the formula (I), in an organic solvent preferably selected from tetrahydrofuran, diethyl ether, diisopropyl ether, benzene, dioxane, acetone and ethyl acetate, at a temperature between room temperature and the refluxing temperature of the solvent selected, these temperatures being inclusive, to lead to a derivative of formula (I/A), a special case of the compounds of formula (I) for which G denotes an oxygen atom, A a group NDE and B a cyano group,

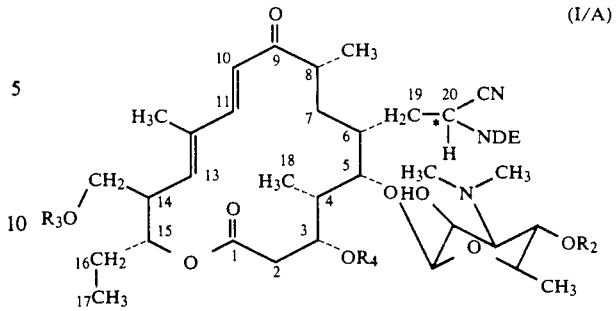
(I/A)

in which formula:

D, E and R₄ have the same definition as in the formula (I) and R₂ and R₃ the same meaning as in the compound (II), (II/2a) or (II/2b) selected, the (R) and (S) isomers of which are separated, if so desired, by a conventional technique such as chromatography on a silica column or fractional crystallization, or, in the case where A and B simultaneously denote a group =N⁺(O⁻)—D, with a compound of formula HO—NHD in which D has the same definition as in the formula (I), or alternatively and preferably with a salt of such a product with a strong acid (hydrochloride, hydrobromide, etc.), in an organic solvent preferably selected from lower aliphatic alcohols, ethyl acetate and acetonitrile, in the presence of a base such as, for example, pyridine, triethylamine or an alkali metal salt such as sodium acetate or sodium hydrogen carbonate or potassium hydrogen carbonate or sodium carbonate or potassium carbonate or calcium carbonate, to lead to a compound of formula (I/B):

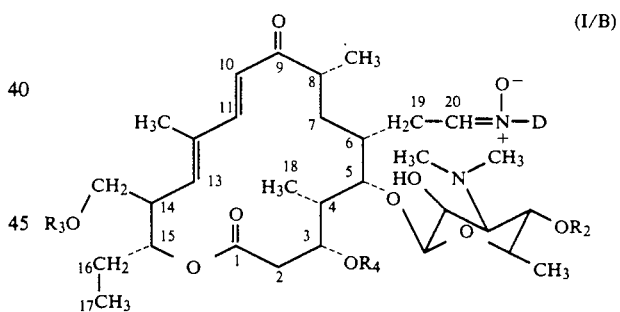
(I/B)

a special case of the compounds of formula (I) in which G denotes an oxygen atom and A and B simultaneously denote a group=N⁺—(O⁻)—D, in which formula R₄ and D have the same meaning as in the formula (I) and R₂ and R₃ the same meaning as in the formula (II), (II/2a) or (II/2b) of the derivative selected, which compounds of formula (I/A) or (I/B) is treated, if so desired, in the presence of a base such as, for example, pyridine, triethylamine or an alkali metal salt such as sodium acetate or sodium hydrogen carbonate or potassium hydrogen carbonate or sodium carbonate or potassium carbonate or calcium carbonate, with a compound of formula (V):

$$H_2N-O-R_1 \qquad (V)$$

in which R₁ has the same meaning as in the formula (I), or alternatively and preferably with a salt of such a product with a strong acid (hydrochloride, hydrobromide, etc.), to obtain, after purification, if desired, by chromatography on a silica column, a compound of formula (I/D):

$$\text{(I/D)}$$

a special case of the compounds of formula (I) in which G denotes a group $$N\sim O-R_1,$$

A, B and $R_4$ have the same meaning as in the compounds (I/A) or (I/B) and $R_2$ and $R_3$ the same meaning as in the formula (II), (II/2a) or (II/2b) of the compounds selected, which is optionally purified by chromatography on a silica column using a suitable solvent mixture such as, for example, a methylene chloride/methanol mixture, and which can, if so desired:

either be salified with a pharmaceutically acceptable acid, or be separated into its isomers and then, if necessary, salified with a pharmaceutically acceptable acid.

The compounds of formula (I) possess advantageous pharmacological properties.

In particular, these compounds are active against gram+cocci and gram−cocci, gram+bacilli (clostridia), certain gram−bacilli, Haemophilus (e.g. *Haemophilus influenzae*), *Neisseria gonorrhoeae*, Brucella, Bordetella, anaerobic bacteria, mycoplasmata, rickettsiae and miyagawanellae (Chlamydia), spirochetes, protozoa and certain dermofungi.

More especially, the compounds of formula (I) possess very good antibiotic activity against pneumococci, staphylococci and streptococci. This spectrum of activity makes the compounds of formula (I) especially advantageous in the treatment of a large number of conditions; among these, it is possible to mention, by way of example, pneumococcal infections such as bronchitis, brucellosis and diphtheria, gonococcal infection, pneumonia, streptococcal infections such as acute angina, otitis, scarlet fever, sinusitis, staphylococcal infections such as staphylococcal septicemia, anthrax, erysipelas, pyoderma, acute staphylococcal infections, bronchopneumonia and plumonary suppurations.

In addition, the compounds of the present invention, by virtue of their structure, are likely to prove advantageous on account of their lack of hepatic or gastrointestinal toxicity, and this distinguishes them favorably from other families of antibiotic compounds.

The subject of the present invention is also pharmaceutical compositions containing the products of formula (I) or one of their addition salts with a pharmaceutically acceptable acid, alone or in combination with one or more pharmaceutically acceptable, non-toxic, inert vehicles or excipients.

Among the pharmaceutical compositions according to the invention, those which are suitable for parenteral, nasal, rectal, perlingual, ocular or respiratory administration may be mentioned more especially, and in particular injectable preparations, aerosols, eye or nose drops, simple or sugar-coated tablets, sublingual tablets, sachets, packets, gelatin capsules, sublingual preparations, bars, suppositories, creams, ointments, skin gels, and the like.

The pharmaceutical compositions according to the invention may also be presented in the form of a lyophilized powder for dissolution at the time of use in a suitable solvent, in particular pyrogen-free sterile water.

The appropriate dosage varies according to the patient's age and weight, the administration route and the nature of the therapeutic indication and of any associated treatments, and ranges between 1 centigram and 4 grams per dose or per application.

The examples which follow illustrate the invention and in no way limit the latter.

The $^{13}C$ and $^1H$ nuclear magnetic resonance spectra were recorded using TMS as internal reference.

The starting material used in the synthesis of the compounds of formula (I) is tylosin, which is known in the literature.

EXAMPLE 1

(RS)-20-Dibenzylamino-20-Cyano-20-Deoxotylosin 9.16 g (10 mmol) of tylosin and 2 ml (12 mmol) of diethyl cyano phosphonate are dissolved in 200 ml of anhydrous tetrahydrofuran. 4.4 ml (22 mmol) of N,N-dibenzylamine are added and the mixture is stirred at room temperature for 8 hours. The reaction medium is evaporated on a water bath under vacuum and the residue obtained is purified by flash chromatography on a silica 60 column, using a 30:1:0.05 methylene chloride/methanol/ammonia solution mixture as eluent.

Yield: 62%

Spectral characteristics: $^1H$ NMR ($\delta$=ppm)

$\delta$=7.20 to 7.50 ppm: complex: aromatic

EXAMPLE 2

(RS)-(9E+9Z)-9-Benzyloxyimino-20-Dibenzylamino-20-Cyano-9,20-Dideoxotylosin

STAGE A: (RS)-20-DIBENZYLAMINO-20-CYANO-20-DEOXOTYLOSIN

See Example 1.

STAGE B: (RS)-(9E+9Z)-9-BENZYLOXYIMINO-20-DIBENZYLAMINO-20-CYANO-9,20-DIDEOXOTYLOSIN 1.12 g (1 mmol) of (RS)-20-dibenzylamino-20-cyano-20-deoxotylosin, obtained above, are dissolved in 13 ml of anhydrous pyridine. 480 mg (3 mmol) of benzyloxyamine hydrochloride are added and the reaction mixture is stirred at room temperature for 4 days. Ice is added and the mixture is extracted with methylene chloride. The organic phase is dried over sodium sulfate, filtered and evaporated to dryness and the residue obtained is purified by flash chromatography on a silica 60 column, using a 40:1:0.05 methylene chloride/methanol/ammonia solution mixture as eluent.

Yield: 45%

Spectral characteristics: $^1H$ NMR ($\delta$=ppm)

$\delta$=7.3 to 7.6 ppm: complex: aromatic

EXAMPLE 3

(RS)-(9E+9Z)-9-Methoxyimino-20-Dibenzylamino-20-Cyano-9,20-Dideoxotylosin

Using the procedure described in Example 2, but replacing benzyloxyamine hydrochloride in stage B by methoxyamine hydrochloride, the expected product is obtained.

Elution solvent for the chromatography on a silica column: methylene chloride/methanol/ammonia solution, 30:1:0.05.

Yield: 45%

Spectral characteristics: $^1$H NMR ($\delta$=ppm)
$\delta$=3.30 ppm: singlet: 3H, CH$_3$, N—O—$\underline{CH_3}$

EXAMPLE 4

(RS)-(9E+9Z)-9-Hydroxyimino-20-Dibenzylamino-20-Cyano-9,20-Dideoxotylosin

Using the procedure described in Example 3, but replacing methoxyamine hydrochloride by hydroxylamine hydrochloride, the expected product is obtained.

EXAMPLES 5 TO 7

In the same manner as in Example 3, replacing methoxyamine hydrochloride by:
EXAMPLE 5: O-allylhydroxylamine hydrochloride,
EXAMPLE 6: O-ethylhydroxylamine hydrochloride,
EXAMPLE 7: para-nitrobenzyloxyamine hydrochloride,
the following are obtained:
EXAMPLE 5: (RS)-(9E+9Z)-9-Allyloxyimino-20-Dibenzylamino-20-Cyano-9,20-Dideoxotylosin
EXAMPLE 6: (RS)-(9E+9Z)-9-Ethyloxyimino-20-Dibenzylamino-20-Cyano-9,20-Dideoxotylosin
EXAMPLE 7: (RS)-(9E+9Z)-9-(Para-Nitrobenzyloxyimino)-20-Dibenzylamino-20-Cyano-9,20-Dideoxotylosin

EXAMPLE 8

20-Deoxotylosin 20-N-Benzyl Nitrone 1.92 g (2.09 mmol) of tylosin base are dissolved in 50 ml of ethanol. 250 mg of sodium bicarbonate and 335 mg (2.09 mmol) of N-benzylhydroxylamine hydrochloride are added. The reaction mixture is stirred at room temperature for 1 h 30 min and evaporated on a water bath under vacuum. The residue obtained is purified by flash chromatography on a silica 60 column, using a 20:1:0.05 methylene chloride/methanol/ammonia solution mixture as eluent.

Yield: 75%

Spectral characteristics: $^1$H NMR ($\delta$=ppm)
$\delta$=4.8 ppm: singlet: 2H, $\underline{CH_2}$, —C$_6$H$_5$

EXAMPLE 9

(9E+9Z)-9-Benzyloxyimino-9,20-Dideoxotylosin 20-N-Benzyl Nitrone

STAGE A: 20-DEOXOTYLOSIN 20-N-BENZYL NITRONE
Obtained in Example 8.
STAGE B: (9E+9Z)-9-BENZYLOXYIMINO-9,20-DIDEOXOTYLOSIN 20-N-BENZYL NITRONE 500 mg (0.49 mmol) of 20-deoxotylosin 20-N-benzyl nitrone, obtained in the preceding stage, are dissolved in 10 ml of anhydrous pyridine. 235 mg (1.47 mmol) of benzyloxyamine hydrochloride are added. The reaction mixture is stirred for 2 hours at room temperature. Ice is then added and the mixture is extracted with methylene chloride. The organic phase is dried over sodium sulfate, filtered and evaporated to dryness. The crude residue is purified by chromatography on a silica 60 column, using a 20:1:0.05 methylene chloride/methanol/ammonia solution mixture as eluent.

Yield: 55%

Spectral characteristics: $^1$H NMR ($\delta$=ppm)
$\delta$=5.10, 2×2H, 2CH$_2$ (CH$_2$C$_6$H$_5$)
$\delta$=7.40, 2×5H, aromatic

EXAMPLES 10 to 11

Using the procedure described in Example 9, and replacing benzyloxyamine hydrochloride in stage B by:
EXAMPLE 10: methoxyamine hydrochloride
EXAMPLE 11: para-nitrobenzyloxyamine hydrochloride
the following are obtained:
EXAMPLE 10: (9E+9Z)-9-Methoxyimino-9,20-Dideoxotylosin 20-N-Benzyl Nitrone
EXAMPLE 11: (9E+9Z)-9-(Para-Nitrobenzyloxyimino)-9,20-Dideoxotylosin 20-N-Benzyl Nitrone

EXAMPLE 12

(R)-20-Benzylamino-20-Cyano-20-Deoxotylosin and (S)-20-Benzylamino-20-Cyano-20-Deoxotylosin 500 mg of tylosin base (0.55 mmol) and 0.11 ml (0.66 mmol) of diethyl cyanophosphonate are dissolved in 10 ml of anhydrous tetrahydrofuran. 0.13 ml of benzylamine is added and the reaction mixture is stirred at room temperature for 6 hours. The tetrahydrofuran is evaporated off on a water bath under vacuum. The crude residue is purified by chromatography on a silica 60 column, using a 40:1:0.05 methylene chloride/methanol/ammonia solution mixture as eluent; each of the two isomers (R) and (S), is obtained in a 20% yield for each isomer, followed by a mixture of the two isomers.

Overall yield: 50%

Spectral characteristics: $^1$H NMR ($\delta$=ppm)
$\delta$=7.30 ppm: complex: aromatic rings.

EXAMPLE 13

(R)-(9E+9Z)-9-Benzyloxyimino-20-Benzylamino-20-Cyano-9,20-Dideoxotylosin

STAGE A: (R)-20-BENZYLAMINO-20-CYANO-20-DEOXOTYLOSIN
See Example 12.
STAGE B: (R)-(9E+9Z)-9-BENZYLOXYIMINO-20-BENZYLAMINO-20-CYANO-9,20-DIDEOXOTYLOSIN 1.4 mg (1.36 mmol) of (R)-20-benzylamino-20-cyano-20-deoxotylosin are dissolved in 13 ml of pyridine, and 650 mg (4.1 mmol) of benzyloxyamine hydrochloride are added. The reaction mixture is stirred for 3 days at room temperature, ice is added and the mixture is extracted with methylene chloride. The extract is dried over sodium sulfate. It is filtered and evaporated to dryness. The residue obtained is purified by chromatography on a silica 60 column, using a 40:1:0.05 methylene chloride/methanol/ammonia solution mixture as eluent.

Yield: 53%

Spectral characteristics: $^1$H NMR ($\delta$=ppm)
$\delta$=7.30 ppm: complex: aromatic rings.

EXAMPLE 14

(S)-(9E+9Z)-9-Benzyloxyimino-20-Benzylamino-20-Cyano-9,20-Dideoxotylosin

Using the procedure described in Example 13, but employing (S)-20-benzylamino-20-cyano-20-deoxotylosin instead of (R)-20-benzylamino-20-cyano-20-deoxotylosin after stage A, the expected product is obtained.

Yield: 40%

Spectral characteristics: $^1$H NMR ($\delta$=ppm)
$\delta$=7.30 ppm: complex: aromatic rings.

EXAMPLE 15

(R)-(9E+9Z)-9-Methyloxyimino-20-Benzylamino-20-Cyano-9,20-Dideoxotylosin

STAGE A: (R)-20-BENZYLAMINO-20-CYANO-20-DEOXOTYLOSIN

Obtained in Example 12.

STAGE B: (R)-(9E+9Z)-9-METHOXYIMINO-20-BENZYLAMINO-20-CYANO-9,20-DIDEOXOTYLOSIN 1 g (0.97 mmol) of (R)-20-benzylamino-20-cyano-20-deoxotylosin is dissolved in 10 ml of pyridine. 250 mg (3 mmol) of methoxyamine hydrochloride are added. The reaction mixture is stirred for 8 days at room temperature. Ice is added, the mixture is extracted with methylene chloride, the extract is dried over sodium sulfate, filtered and evaporated to dryness and the residue is purified by flash chromatography on a silica 60 column, using a 40:1:0.05 methylene chloride/methanol/ammonia solution mixture as eluent.

Yield: 25%

Spectral characteristics: $^1$H NMR ($\delta$=ppm)
$\delta$=7.35 ppm: complex: aromatic.

EXAMPLE 16

(S)-(9E+9Z)-9-Methyloxyimino-20-Benzylamino-20-Cyano-9,20-Dideoxotylosin

Using the procedure described in Example 15, but replacing (R)-20-benzylamino-20-cyano-20-deoxotylosin in stage A by (S)-20-benzylamino-20-cyano-20-deoxotylosin, the expected product is obtained.

EXAMPLES 17 AND 18:

(R)-(9E+9Z)-9-(Para-Nitrobenzyloxyimino)-20-Benzylamino-20-Cyano-9,20-Dideoxotylosin and (S)-(9E+9Z)-9-(Para-Nitrobenzyloxyimino)-20-Benzylamino-20-Cyano-9,20-Dideoxotylosin By replacing methoxyamine hydrochloride in Examples 15 and 16 by para-nitrobenzyloxyamine hydrochloride, the expected products are obtained.

EXAMPLE 19

(9E+9Z)-9-Benzyloxyimino-20-Dibenzylamino-20-Cyano-9,20-Dideoxodemycarosyldemycinosyltylosin

STAGE A: DEMYCAROSYLTYLOSIN 4 g (0.004 mmol) of tylosin base in 80 ml of 0.2N hydrochloric acid are stirred for 4 hours at room temperature. The reaction medium obtained is washed with dichloromethane and the aqueous phase is separated and adjusted to pH 8.0. The latter phase is extracted twice with 120 ml of dichloromethane, and the organic phases are combined, dried over sodium sulfate and evaporated. The residue consists of demycarosyltylosin.

Yield: 94%

Spectral characteristics: Mass spectrometry: [M-H]$^+$: M/Z: 772

STAGE B: DEMYCAROSYLDEMYCINOSYLTYLOSIN 5 g (0.0065 mmol) of demycarosyltylosin, obtained in stage A, are dissolved in 110 ml of 0.5N hydrochloric acid and the mixture is stirred for approximately 27 hours at 75° C. The reaction medium is washed with dichloromethane. The aqueous phase is recovered, adjusted to pH 8 and extracted twice with 120 ml of dichloromethane. The organic phase is dried over sodium sulfate and evaporated. The residue is chromatographed on silica gel (eluent: CH$_2$Cl$_2$/MeOH/NH$_4$OH, 10:1:0.05) to obtain the gel (eluent: CH$_2$Cl$_2$/MeOH/N-H$_4$OH, 10:1:0.05) to obtain the expected product.

Yield: 20%

Spectral characteristics: Mass spectrometry: [M-H]$^+$: M/Z: 598

STAGE C: (9E+9Z)-9-BENZYLOXYIMINO-20-DIBENZYLAMINO-20-CYANO-9,20-DIDEOXODEMYCAROSYLDEMYCINOSYLTYLOSIN

Using the procedure described in Example 2, but replacing tylosin by demycarosyldemycinosyltylosin, the expected product is obtained.

EXAMPLE 20

(9E+9Z)-9-Benzyloxyimino-9,20-Dideoxodemycarosyldemycinosyltylosin20-N-Benzyl Nitrone Using the procedure described in Example 9, but replacing tylosin in stage A by demycarosyldemycinysyltylosin obtained in stage B of Example 19, the expected product is obtained.

EXAMPLE 21

Study of the Activity of the Products of the Invention Against Various Bacterial Strains Determination of the minimal inhibitory concentrations (MIC) is performed:

for staphylococci and enterococci (group D streptococci), in MUELLER HINTON agar or liquid medium;

for Haemophilus, non-D streptococci and *Neisseria gonorrhoeae*, determination of the MIC is performed according to the dilution method in cooked blood agar medium enriched with Polyvitex* mixture. Culturing is carried out in a CO$_2$-enriched atmosphere.

Reading of the MIC is performed after 18 hours' incubation at 37° C.

The products are tested in a concentration range from 0.125 to 256 mg/l (successive doubling dilutions).

The minimal inhibitory concentrations are of the order of:

1 mg. 1$^{-1}$ for *Staphylococcus aureus*, groups B, C, 0.5 mg. 1$^{-1}$ for group A streptococci;

0.1 mg. 1$^{-1}$ for *Neisseria gonorrhoeae*.

These studies collectively show the advantageous antibiotic activity of the product of the invention, in respect of both the intensity of its activity and also the breadth of its spectrum of action.

EXAMPLE 22

Pharmaceutical Composition: Tablet

Tablets containing 100 mg of (9E+9Z)-9-benzyloxyimino-20-dibenzylamino-20-cyano-9,20-dideoxotylosin.

| | |
|---|---|
| (9E + 9Z)-9-Benzyloxyimino-20-dibenzylamino-20-cyano-9,20-dideoxotylosin | 100 g |
| Wheat starch | 70 g |
| Corn starch | 60 g |
| Lactose | 60 g |
| Magnesium stearate | 9 g |
| Silica | 4 g |
| Hydroxypropylcellulose | 7 g |

Preparation formula for 1000 tablets.

We claim:

1. A compound of the formula (I):

(I)

in which:
either:
A denotes a group in which D and E, which may be identical or different, denote, independently of one another, a hydrogen atom or a linear or branched lower alkyl radical which may be substituted with a phenyl group, and B denotes a cyano group,
or
A and B together denote a group $=N^+(O^-)-D$ in which D has the meaning given above,
G denotes an oxygen atom or a group of the formula $N \sim O-R_1$ in which $R_1$ denotes a hydrogen atom, a linear or branched lower alkyl group or a linear or branched lower alkenyl group, which lower-alkyl or lower alkenyl groups may be substituted with a phenyl group which itself may be substituted with a nitro group,
the sign
occurring in the definition of G meaning that the oxime or oxime ether group can be in the syn or anti form,
$R_2$ denotes
a hydrogen atom,
or a radical of the formula:

in which $R'_2$ denotes a hydrogen atom, a linear or branched lower alkyl radical, or a linear or branched lower acyl radical,
$R_3$ denotes a hydrogen atom or a group:

and
$R_4$ and $R_5$ denote, independently of one another:
a hydrogen atom,
or a linear or branched lower alkyl radical,
lower alkyl and lower alkenyl radicals having 1 to 6 carbon atoms, inclusive or an isomer or a diastereoisomer thereof, or an acid addition salt thereof with a pharmaceutically-acceptable acid.

2. A compound as claimed in claim 1, in which A denotes a group as defined in claim 1, and B denotes a cyano group, or an isomer or a diastereoisomer thereof, or an acid addition salt thereof with a pharmaceutically-acceptable acid.

3. A compound as claimed in claim 1, in which A and B simultaneously denote a group $=N^+(O^-)-D$, D being as defined in claim 1, or an isomer or a diastereoisomer thereof, or an acid addition salt thereof with a pharmaceutically-acceptable acid.

4. A compound as claimed in claim 1, in which G denotes an oxygen atom, or an isomer or a diastereoisomer thereof, or an acid addition salt thereof with a pharmaceutically-acceptable acid.

5. A compound as claimed in claim 1, in which G denotes a group $N \sim OR_1$, or an isomer or a diastereoisomer thereof, or an acid addition salt thereof with a pharmaceutically-acceptable acid.

6. A compound as claimed in claim 1 which is (9E+9Z)-9-benzyloxyimino-20-dibenzylamino-20-cyano-9,20-dideoxotylosin.

7. A compound as claimed in claim 1 which is (9E+9Z)-9-benzyloxyimino-9,20-dideoxotylosin 20-N-benzyl nitrone.

8. A compound as claimed in claim 1 which is (RS)-(9E+9Z)-9-(para-nitrobenzyloxyimino)-20-benzylamino-20-cyano-9,20-dideoxotylosin, or the R or S isomer thereof.

9. A pharmaceutical composition suitable for treating a bacterial infection containing, as active principle, an effective antibacterial amount of at least one compound as claimed in claim 1, in combination with a pharmaceutically-acceptable vehicle or excipient.

10. A method for treating an animal afflicted with a bacterially infections conditions comprising the step of administering to the said animal an amount of a compound of claim 1 which is effective for the alleviation of the said bacterially infections condition.

* * * * *

UNITED STATES PATENT AND TRADEMARK OFFICE
CERTIFICATE OF CORRECTION

PATENT NO. : 5,032,581

DATED : July 16, 1991

Page 1 of 2

INVENTOR(S) : Gabor Lukacs, Catherine Ruggeri-Duchatelle, Aimee Dessinges, Alain Olesker, Maria Laborde and Li Ming It is certified that error appears in the above-identified patent and that said Letters Patent is hereby corrected as shown below:

Title Page [57] ABSTRACT, 5th line from bottom; "∼∼∼" should read -- $\nu\nu$ --

Col. 1, approx. line 33, a little to the right of the middle of the formula; "OHO" should read -- O HO -- (these are two separate substituents)

Col. 1, line 65; "sign      occurring" should read -- sign $\nu\nu$ occurring --

Col. 3, approx. lines 10 and 40 (in both instances), far lower right of the formula; "OR$_2$" should read -- OH -- (in both occurrences)

Col. 4, approx. line 9, a little to the right of the middle of the formula; "OHO" should read -- O HO -- (these are two separate substituents)

Col. 5, approx. line 12, a little to the right of the middle of the formula; "OHO" should read -- O HO -- (these are two separate substituents)

Col. 5, line 59; "plumonary" should read -- pulmonary --

Col. 8, lines 21&22; "-Nitrobenzyloxymino)-" should read -- -Nitrobenzyloxyimino)- --

Col. 11, line 50; "group or" should read -- group, or -- (PA, 10/11/89, pg 1)

Col. 11, approx. line 22, a little to the right of the middle of the formula; "OHO" should read -- O HO -- (these are two separate substituents)

Col. 11, line 55; "the sign" should read -- the sign $\nu\nu$ --

Col. 12, line 64; "bacterially infections conditions" should read -- bacterial infectious condition" (PA, 10/11/89, pg 3)

Col. 12, line 67; "infections" should read -- infectious -- (PA, 10/11/89, pg3)

UNITED STATES PATENT AND TRADEMARK OFFICE
CERTIFICATE OF CORRECTION

PATENT NO. : 5,032,581  
DATED : July 16, 1991  
INVENTOR(S) : Gabor Lukacs, Catherine Ruggeri-Kuchatelle, Aimee Dessinges, Alain Olesker, Maria Laborde and Li Ming It is certified that error appears in the above-identified patent and that said Letters Patent is hereby corrected as shown below:

Title Page [57] ABSTRACT, a little to the right of the middle of the formula; "OHO" should read -- O  HO -- (these are two separate substituents)

Signed and Sealed this

Twenty-third Day of February, 1993

Attest:

STEPHEN G. KUNIN

Attesting Officer            Acting Commissioner of Patents and Trademarks